US008534277B2

(12) United States Patent
Stenzler et al.

(10) Patent No.: US 8,534,277 B2
(45) Date of Patent: Sep. 17, 2013

(54) DEVICE, SYSTEM AND METHOD FOR TARGETING AEROSOLIZED PARTICLES TO A SPECIFIC AREA OF THE LUNGS

(75) Inventors: Alex Stenzler, Long Beach, CA (US); William C. Zimlich, Dublin, OH (US); Gerhard Scheuch, Wohratal (DE); Bernhard Müllinger, Munich (DE); Tobias Kolb, Munich (DE); Tobias Hoffmann, Munich (DE); Andreas Wenker, Landsberg (DE); Axel Fischer, Moischeid (DE); Sascha Roeder, Munich (DE)

(73) Assignee: Activaero GmbH, Gemunden (DE)

( * ) Notice: Subject to any disclaimer, the term of this patent is extended or adjusted under 35 U.S.C. 154(b) by 1430 days.

(21) Appl. No.: 12/183,747

(22) Filed: Jul. 31, 2008

(65) Prior Publication Data

US 2009/0056708 A1     Mar. 5, 2009

(30) Foreign Application Priority Data

Aug. 2, 2007   (EP) ..................... 07113705

(51) Int. Cl.
*A61M 11/00*     (2006.01)
*A61M 15/00*     (2006.01)
*A61M 16/00*     (2006.01)

(52) U.S. Cl.
USPC ................. 128/200.14; 128/203.14

(58) Field of Classification Search
USPC ............. 128/200.14, 203.12, 203.14, 203.15, 128/200.16, 200.23, 203.23, 203.24, 204.21, 128/204.23, 204.26
See application file for complete search history.

(56) References Cited

U.S. PATENT DOCUMENTS

| 5,161,524 | A | * | 11/1992 | Evans | 128/203.15 |
| 5,542,410 | A | * | 8/1996 | Goodman et al. | 128/200.14 |
| 5,568,807 | A | * | 10/1996 | Mecikalski | 128/203.21 |
| 5,608,647 | A | * | 3/1997 | Rubsamen et al. | 700/281 |
| 5,713,349 | A | | 2/1998 | Keaney | |
| 5,813,397 | A | * | 9/1998 | Goodman et al. | 128/200.14 |
| 5,839,430 | A | * | 11/1998 | Cama | 128/200.14 |
| 5,842,468 | A | * | 12/1998 | Denyer et al. | 128/200.23 |
| 5,906,202 | A | | 5/1999 | Schuster et al. | |
| 6,024,089 | A | * | 2/2000 | Wallace et al. | 128/204.21 |
| 6,269,810 | B1 | * | 8/2001 | Brooker et al. | 128/203.12 |
| 6,435,175 | B1 | * | 8/2002 | Stenzler | 128/200.14 |

(Continued)

FOREIGN PATENT DOCUMENTS

| DE | 2936433 | 6/1980 |
| DE | 4009067 | 12/1991 |

(Continued)

OTHER PUBLICATIONS

European Search Report from European application No. 07113705.3, dated Jan. 24, 2008, 3 pp.

*Primary Examiner* — Kristen Matter
(74) *Attorney, Agent, or Firm* — Kagan Binder, PLLC (57) ABSTRACT

The present invention is directed to the administration of aerosolized particles to specific area of the lungs, and in particular to the targeted delivery of aerosolized pharmaceutical formulations to a specific area of the lungs. More specifically, the present invention relates to devices and methods for depositing aerosolized particles to a specific area of the lungs by regulating aerosolizing parameters of the device. The present invention also relates to devices, systems and methods for disease management, where the aerosolizing parameters are adjusted based on monitoring at least one health parameter.

44 Claims, 8 Drawing Sheets

(56) References Cited

U.S. PATENT DOCUMENTS

| | | | |
|---|---|---|---|
| 6,571,791 B2 | 6/2003 | Scheuch et al. | |
| 6,606,989 B1* | 8/2003 | Brand et al. | 128/200.16 |
| 6,606,992 B1* | 8/2003 | Smith et al. | 128/203.15 |
| 6,681,762 B1 | 1/2004 | Scheuch et al. | |
| 2003/0136400 A1* | 7/2003 | Klimowicz et al. | 128/200.16 |
| 2005/0016533 A1* | 1/2005 | Schuler et al. | 128/203.15 |
| 2005/0133024 A1* | 6/2005 | Coifman | 128/200.14 |
| 2005/0217666 A1 | 10/2005 | Fink et al. | |
| 2007/0006883 A1 | 1/2007 | Kolb et al. | |
| 2011/0030681 A1* | 2/2011 | De Vries et al. | 128/203.12 |
| 2011/0308515 A1* | 12/2011 | Snyder et al. | 128/200.21 |

FOREIGN PATENT DOCUMENTS

| | | |
|---|---|---|
| EP | 1245244 | 10/2002 |
| FR | 2783431 | 3/2000 |
| WO | 0050111 | 8/2000 |

* cited by examiner

DEVICE, SYSTEM AND METHOD FOR TARGETING AEROSOLIZED PARTICLES TO A SPECIFIC AREA OF THE LUNGS

REFERENCE TO RELATED APPLICATIONS

This application claims priority to EP Application No. 07113705.3 filed Aug. 2, 2007, entitled DEVICE, SYSTEM AND METHOD FOR TARGETING AEROSOLIZED PARTICLES TO A SPECIFIC AREA OF THE LUNGS, and is incorporated herein by reference.

FIELD OF THE INVENTION

The present invention is directed to the administration of aerosolized particles to specific areas of the lungs, and in particular to the targeted delivery of aerosolized pharmaceutical formulations to specific areas of the lungs. More specifically, the present invention relates to devices and methods for depositing aerosolized particles to specific areas of the lungs by regulating aerosolization parameters of the device. The present invention also relates to devices, systems and methods for disease management, where the aerosolization parameters are adjusted based on monitoring at least one health parameter.

BACKGROUND OF THE INVENTION

Effective drug delivery to a patient is a critical aspect of any successful drug therapy. Of particular interest to the invention are pulmonary delivery techniques which rely on the inhalation of a pharmaceutical formulation by the patient so that a drug or active agent within the formulation can reach the lungs. Pulmonary delivery techniques can be advantageous for certain respiratory diseases in that it allows selective delivery of optimal concentrations of pharmaceutical formulations to the airways while causing less side effects than systematic administration. Nevertheless, many patients have experienced significant side effects caused by the necessary dosage for drugs commonly used in pulmonary delivery. Therefore, there is still a need to eliminate undesirable side effects, which in some case may include an increased risk for heart attack. For reducing these side effects, a pharmacologic approach has been taken. However, in some cases, the new found drugs are significantly more expensive thereby representing a major disadvantage to patients from poorer socio-economic populations. Therefore, it would be advantageous to provide an alternative to the pharmacologic approach, whereby commonly used drugs can be delivered in an effective manner without the undesirable side effects.

It has been found that the efficacy of drug delivery can be improved by targeting the aerosolized medication to certain areas of the lungs. Delivery and deposition of aerosols are determined by both the aerosol characteristics and by patient's breathing characteristics. Many existing inhalation devices can deliver aerosolized particles to the lungs, yet lack the ability to target the delivery to certain areas of the lungs.

U.S. Pat. No. 5,906,202 describes a device and method for directing aerosolized mist to a specific area of the respiratory tract. By determining the particle size of the aerosols in combination with determining the volume of aerosol and aerosol free air allowed into the respiratory tract, it is possible for the described device to target a particular area of the respiratory tract. The device can allow the subject to inhale a predetermined volume of unaerosolized air followed by a predetermined volume of aerosol after which flow can be shut off completely or followed by additional aerosol free air. To this end, inspiratory flow rate measurements are made in order to determine a desired flow rate. The device then comprises a switch for releasing the predetermined volume of aerosol and aerosol free air at the desired flow rate. However, if the subject is unable to control their inspired flow rate to the set value, she/he will never receive the drug. This represents a disadvantage. It is also well known that the inspired flow can affect aerosol deposition independent of inspired volume. Since the described device requires that the subject breathe at a specific flow to trigger the aerosol, if the subject changes their flow immediately at the point of aerosol triggering, the deposition can be significantly altered, thereby representing another disadvantage. Further, there is still a need for a simpler device which enables lower costs for manufacture.

SUMMARY OF THE INVENTION

It is an object of the present invention to provide improved devices, methods and systems which overcome the various aforementioned drawbacks of the prior art.

It is also an object of the present invention to provide a method and device for depositing aerosolized particles to specific areas of the lungs which enables effective treatment using lower doses of the drug.

It is also an object of the present invention to provide a disease management system which enables the aerosolization parameters of the device to be adapted depending on measurement of at least one health parameter. For example, the measurement may be a spirometer for measuring a pulmonary function parameter indicative of the subject's inhalation or exhalation capacity. The monitor may also be a cardio-sensor for measure heart rate. The monitor may also be a glucose sensor for invasively or non-invasively measuring blood glucose levels.

The present invention relates to novel methods and devices for targeting aerosolized particles, preferably aerosolized pharmaceutical formulations, to specific areas of the lungs. The pharmaceutical formulations that may be aerosolized include powdered medicaments, liquid solutions or suspensions and the like and may include an active agent.

The inventors have found that effective targeting of aerosol particle deposition can be achieved by presetting certain aerosolization parameters of the device. The methods and devices of the present invention enable effective treatment to be maintained with notable reduction in the normally required amount of drug thereby possibly reducing or eliminating side effects. Targeting can be achieved by altering aerosol parameters, such as volume, particle size, timing and flow rate. As for timing, the present invention allows or introduces particle free air for a first predefined time period, then introduces a certain amount of aerosolized particles, also commonly referred to as an aerosol bolus, followed by a second predefined period of aerosol particle free air.

The first predefined period of particle free air is optional, as the device can be adapted to activate the introduction of the aerosolized particles or aerosol bolus upon sensing the subject's inhalation. This might be desirable in cases where the aerosolized particles should be deposited to the lower regions (alveolar regions) of the lungs. The object of introducing particle free air in the first predefined period is to direct air to the lower regions of the lungs. This helps to support ventilation (removal of carbon dioxide). The volume capacity of the lower regions of the lungs will vary depending on the subject. The first time period could represent the amount of estimated time that it takes to fill the lower regions of the lungs. This time period is generally preset depending on the subject's data and can be adjusted depending on what best suits the subject.

For targeting of bronchial areas within the lungs preferably, the first predefined time period of aerosol particle free air is set to be up to about 10 seconds. Most preferably, the first predefined time period of aerosol particle free air is up to 6 seconds, in particular 1 to 5 seconds, 2 to 4 seconds. Preferably, the first predefined time period enables a predefined volume of aerosol particle free air, the predefined volume being up to 6 liters. Most preferably, the predefined volume of aerosol particle free air is about 0.1 to 3 liters, in particular 0.1 to 0.8 liters.

For targeting of peripheral areas within the lungs, the first predefined time period of aerosol particle free air is set to be up to 3 seconds. Most preferably, the first predefined time period of aerosol particle free air is up to 0.2 seconds, in particular up to 0.06 seconds. Preferably, the first predefined time period enables a predefined volume of aerosol particle free air, the predefined volume being up to 0.4 liters. Most preferably, the predefined volume of aerosol particle free air is up to 0.04 liters, in particular 0.01 liters.

The device is adapted to administer a desired volume of aerosolized particles and can be adapted to administer the aerosolized particles within a predetermined time period. This volume is determined by the amount of pharmaceutical formulation that should be deposited in the lungs. Preferably, the predefined volume of aerosolized particles or aerosol bolus is set to be up to about 3000 ml. Most preferably, the pre-set volume of aerosolized particles is about 50 to 1300 ml. in particular 100 to 300 ml. The predefined volume of aerosolized particles can be introduced into the flow path for a preset time period. The loading dosage of pharmaceutical formulation to be aerosolized corresponding to the aerosol bolus can vary. Preferably, the amount of pharmaceutical formulation is less than 500 mg, most preferably about 1 to 600 µg, in particular about 10 to 300 µg.

After release of the predefined volume of aerosolized particles, a volume of aerosol particle free air is introduced for a predefined time period. The object of this time period of particle free air is to clear the upper region and extrathoracic airway region, respectively, (e.g., mouth, pharynx, and trachea) of the lungs to thereby drive the aerosol bolus to the central region (bronchial) or peripheral region of the lungs. Preferably, this predefined time period of aerosol particle free air is set to be up to about 10 second. Most preferably, this time period of aerosol particle free air is about 0.2 to 8 seconds, in particular 0.3 to 2 seconds. Preferably, this predefined time period enables a predefined volume of aerosol particle free air, the predefined volume being preferably up to 3 liters. Most preferably, this volume of aerosol particle free air is about 0.01 to 0.8 liters, in particular 0.05 to 0.3 liters.

The length of the time periods can vary depending on which area of the lung is targeted for deposition.

The present invention provides a device comprising a flow rate limiter or controller for limiting inhalation flow rate in a flow path to a preset flow rate range; and a timer to initiate, once a subject begins inhalation and has inhaled a first predefined time period of aerosol particle free air, a predefined volume of aerosolized particles to be introduced into the flow path, and to initiate after said predefined volume of aerosolized particles a second predefined time period of aerosol particle free air, such that the aerosolized particles are directed to the central airways of the lungs.

The timer of the present invention serves to initiate the periods of aerosol particle and particle free flow. The timer can be in any form suitable in the field. Preferably, the timer is an electronic device which can be programmed or set with the predefined time periods. Preferably, the timer is adapted to indicate to the subject to stop inhaling after the subject has inhaled for the second predefined time period of aerosol particle free air or the device may further comprise an indicator to alert the subject to stop inhaling after the subject has inhaled for the second predefined time period of aerosol particle free air. The indicator may be an audible indicator that produces a tone or a visual indicator that flashes a light or changes color for alerting the subject.

The flow limiter or controller of the present invention is for limiting or controlling inhalation flow rate in a flow path to be in a preset flow rate range. Preferably, the flow rate limiter is a discretely or continuously variable flow limiter or a controllable valve. Most preferably, the flow limiter has the features of the flow limiting device of U.S. Pat. No. 6,681,762, the control means of U.S. Pat. No. 6,571,791, or the controllable valve of US 2007/0006883 A1, the disclosures of which are incorporated herein by reference.

In one embodiment of the flow limiter, the inspiratory flow is controlled by rigid and flexible walls that change cross sectional area as a function of the differential pressure across the orifices.

For example, U.S. Pat. No. 6,681,762 describes a preferred embodiment of the flow limiter, wherein the flow passage is configured to have a flat elongate cross-section which is formed to have opposing large-area walls. This configuration enhances the inward bending of the walls for a reduction of the cross-section of the passage. The opposing walls are open on their outside, at least in the central area between the aspiration and inhalation orifices, to the environment, with each wall having preferably one chamber section on its outside, which is open via a bore to the environment, at least in the central area between the aspiration and inhalation orifices. With these structural provisions the required pressure equalization is ensured when the walls are contracted.

In another embodiment, the flow limiter comprises a stratified structure for the flow passage, which comprises preferably a closed wall, a frame-shaped partition of the same size, and a wall of equal size with an aspiration and inhalation orifice, with the opposite walls being fastened on the sides of their edges in the housing. Any flexible and biologically tolerable material is suitable for configuring the flow passage, which material is flexible and can also be returned into its original shape after bending. It is preferred that at least the large-area passage walls, preferably also the partition, consist of silicone mats or foils whilst the housing is made of a preferably biologically tolerable material.

In another embodiment of the flow limiter, the material layers of the flow passage are fastened for exchange between two housing sections. With such a structure, it is possible in a simple manner to use one flow limiter for different flow rate limiting parameters with a correspondingly associated flow passage. Each of the large-area passage walls has preferably the same thickness.

In another embodiment of the flow limiter, provisions are made for a flow rate limitation independent of the environmental pressure, wherein each wall comprises on its outside a chamber section with a bore at least in the central area between the aspiration and inhalation orifices, which bores communicate with the aspiration orifice through a passage or a hose, respectively. With these provisions the differential pressure between the aspiration and inhalation orifices is measured, which is decisive for control, and flow rate limitation could also be operated in a closed system.

According to a further embodiment of the flow limiter, the flow passage may have an annular cross-section, instead of a flat elongate cross-section, with the flow passage being preferably symmetrically disposed in a cylindrical housing at a spacing from the inside cylinder wall, between radial disks. These retainer disks are preferably provided with aspiration and inhalation orifices having the shape of ring segments, with the retainer disk having pressure equalizing bores for the cylindrical inside area and the annular zone surrounding the flow passage. This annular flow passage is preferably formed of silicone.

In another embodiment of the flow limiter, provisions are made for the formation of the flow region between a central inhalation orifice and aspiration orifices radially surrounding them which region presents star-shaped or radial webs extending from a common bottom surface to the flexible wall and forming flow passages which can be restricted. With these provisions, the device can be designed with an extraordinarily compact structure that is easy to manufacture and to replace.

The webs forming flow passages may have different lengths so that in the region of the longer webs a wider flow passage will be formed which then splits into several flow passages at intermediately arranged shorter webs. The cross-section of the webs may be constant in a radial direction. The webs flare outwardly over their width, with one aspiration orifice being preferably provided between two adjacent webs.

In another embodiment, the flow limiter has a disk-shaped basic body wherein webs are integrally formed between flat recesses. Inhalation orifices are formed on the edge side in the recesses. The flow limiter has a thin flexible mat with a central aspiration orifice, which rests on the webs and is fastened in the edge region of the basic body. The mat may be adhesively fastened or welded, respectively, or clamped by means of an annular assembly element in the edge region of the basic body. The thin flexible mat is preferably made of silicone, silicone rubber, Viton, latex, natural rubber or any other elastomer.

The flow limiter of the present invention may also be a control means as described in U.S. Pat. No. 6,571,791, wherein flow rate limiting is achieved by an adjustable channel height. In one embodiment, a flow channel is delimited preferably by two flexible walls arranged in parallel and spaced apart from each other, which, depending on the negative pressure, bends towards the inside and thus reduce the cross section of the channel, thereby limiting the flow. Other embodiments of the control means described in U.S. Pat. No. 6,571,791 are also suitable as flow limiters for the present invention and are enclosed herein by reference.

The flow limiter of the present invention may also be a controllable valve as disclosed in US 2007/0006883. In one embodiment, the controllable valve comprise a housing, a membrane, an optional pressure plate, a closure element, a set piston and an adjusting screw, wherein the housing is essentially tubular and comprises a plurality of radially arranged webs, one web being longer than the others. On one side of the webs, the housing is designed so as to adjustably receive the set piston. On the opposite side so as to receive the membrane, the optional pressure plate and the closure element. The controllable valve allows for continuous or gradual flow control. Other embodiments of the controllable valve described in US 2007/0006883 are also suitable as flow limiters for the present invention and are enclosed herein by reference.

In one embodiment of the present invention, the flow limiter is a control valve actuated by an inflatable balloon.

In another embodiment of the present invention, the flow limiter is a piezo-controlled flow limiter, for example, comprising a flow channel having a height that is adjustable using a piezoelectric mechanism.

Preferably, the device of the present invention comprises air control means responsive to the timer and adapted to seal the flow path after the subject has inhaled the second predefined time period of aerosol particle free air. Preferably, the air control means is an air shut off valve, air shut off channel, air control valve or the like. Preferably, the device comprises an air control valve for enabling a pre-settable volumetric flow of compressed air. Preferably, the air control means comprises a piezo-controlled valve, diaphragm-activated motor, solenoid, air piston and/or a mechanical valve operable with a timer.

The device of the present invention preferably comprises a sensor in any suitable form for detecting when a subject is inhaling through the flow path. Preferably, the sensor comprises a pressure gauge responsive to suction pressure due to the subject's inhalation. In another embodiment, the sensor comprises a diaphragm responsive to sound waves caused by of the subject's inhaling. The diaphragm is preferably a microphone. In yet another embodiment, the sensor comprises a mechanical switch. In yet another embodiment, the sensor comprises a piezo membrane. Preferably, the sensor is placed at or within the inhaling channel of the device.

The device of the present invention may be designed to receive a variety of detachable components, such as a mouthpiece, nebulizer or the like, and at least one cartridge or the like containing the pharmaceutical formulation.

The device of the present invention may comprise a mouthpiece connected in fluid communication with the inhalation flow path. The mouthpiece may be a permanent part of the housing or a detachable part.

Preferably, the device of the present invention comprises at least one orifice connectable to a source of aerosolized particles. The aerosolized particle source is preferably releasably or detachably connected to the device by any suitable means known in the art. The aerosolized particle source may be a powder dispersion device which utilizes a compressed gas to aerosolize a powder. The aerosolized particle source may be a nebulizer or the like, for aerosolizing solid or liquid particles. The nebulizer may be an ultrasonic nebulizer, a vibrating mesh nebulizer, a jet nebulizer or any other suitable nebulizer or vaporizer known in the field. These nebulizers can be separate components which can be attached to the device before use.

The device of the present invention may also comprise a controller having a memory for storing a subject's individual parameters and/or aerosol depositing parameters. The timer of the present invention may be a component of the controller or a separate component connectable to the controller for receiving and/or sending information and/or data relating to the subject's aerosolization parameters.

The device of the present invention may also comprise a reader for reading a memory means having a subject's individual parameters and/or aerosol depositing parameters stored thereon. The memory means can be in the form of any computer readable storage medium known in the art, such as but limited to a storage stick, memory disk or electronic data card, such as a smart card. The reader can be in any form as known in the art. For example, the reader can be an interface or port, e.g. a USB port or the like, for receiving a storage stick or a drive for receiving a memory or electronic data card.

The device of the present invention may also comprise at least one communication means for receiving and/or sending data associated with a subject's individual parameters and/or aerosol depositing parameters. The communication means may be a wired connection or wireless connection sending and/receiving data via infrared, microwave or radio frequency, optical techniques or any suitable manner known in the art. The communication means may be a telephone connection or jack. This would be advantageous if a health provider, e.g. a doctor, would like to adjust the aerosol parameters from a remote location. For example, the first predefined time period, the second predefined time period, the predefined volume of aerosolized particles and/or the diameter size of the particle to be aerosolized could be adjusted remotely.

The device of the present invention may also comprise at least one monitor for measuring a health parameter. The monitor may be a sensor or component, as known in the art, having suitable means for measuring a physiological factor. For example, the monitor may be a spirometer for measuring a pulmonary function parameter indicative of the subject's inhalation or exhalation capacity. The monitor may also be a cardio-sensor for measure heart rate. The monitor may also be a glucose sensor for invasively or non-invasively measuring blood glucose levels.

The device of the present invention can be in any suitable form, such as a table-top device. Preferably, the device of the present invention is hand-held and portable.

The present invention also relates to disease management methods and systems for monitoring and adapting the parameters for such targeting. The disease management system of the present invention provides at least the advantage of monitoring the health condition of the patient and being able to adjust the present device based on the subject's condition, thereby providing a more effective treatment in most cases.

To this end, the system of the present invention comprises the device of the present invention and at least one monitor for measuring a health parameter, wherein the device is adaptable in response to measurements from one of said at least one monitor.

The monitor may be any apparatus as known in the art for measuring a physiological factor. For example, the monitor may be a spirometer for measuring a pulmonary function parameter indicative of the subject's inhalation or exhalation capacity. The monitor may also be a cardio-sensor for measure heart rate. The monitor may also be a glucose sensor for invasively or non-invasively measuring blood glucose levels. The monitor may be a hand-held device.

Preferably, the system comprises a base station having means for receiving and/or holding the device of the present invention and the at least one monitor. The receiving holding means can be a cradle. The base station preferably has a display for displaying any data and/or information. For example, the status or settings of the base station, device and/or monitor can be displayed. Preferably, the base station has control buttons for changing settings for the base station, device and/or monitor.

The base station of the system also preferably has at least one communication means for receiving and/or sending data associated with a subject's individual parameters and/or aerosol depositing parameters and/or settings for the base station. The communication means may be a wired connection or wireless connection sending and/receiving data via infrared, microwave or radio frequency, optical techniques or any suitable manner known in the art.

The present invention is also directed to methods for operating the aforedescribed devices and systems of the present invention.

Further, the present invention is directed to a method of targeting aerosol particles to a specific area of the lungs comprising at least the steps of a) delivering a predefined volume of aerosolized particles to be inhaled into the flow path; and b) providing a predefined time period of aerosol particle free air into the lungs at a flow rate within the preset flow rate range to move the aerosolized particles to a targeted area of the lungs.

For targeting aerosol particles to the central airways of the lungs, the method of the present invention may comprise a step before step a) of providing a first predefined time period of aerosol particle free air through a flow path into the lungs at a flow rate within a preset flow rate range.

The method may further comprise a step of d) preventing flow through the flow path after providing the second predefined time period of aerosol particle free air.

The method may further comprise a step of d) providing indication to the subject to stop inhaling after providing the second predefined time period of aerosol particle free air for the preset time period.

Preferably, the method comprises a step of detecting when the subject is inhaling through the flow path.

The method of the present invention may further comprise steps of measuring and adapting the first predefined time period, the second predefined time period and/or the predefined volume of aerosolized particles based on measurements of at least one health parameter.

The present invention is also directed to a method for depositing aerosol particles to the central airways of the lungs comprising: a) providing a first predefined time period of aerosol particle free air through a flow path into the lungs at a flow rate within a preset flow rate range; b) delivering a predefined volume of aerosolized particles to be inhaled into the flow path; and c) providing a second predefined time period of aerosol particle free air into the lungs at a flow rate within the preset flow rate range to move the aerosolized particles out of the upper airway region.

Preferably, the method further comprises d) preventing flow through the flow path after providing the second predefined time period of aerosol particle free air. Preferably, the method comprises d) providing indication to the subject to stop inhaling after providing the second predefined time period of aerosol particle free air for the preset time period.

The method may also comprise detecting when the subject is inhaling through the flow path.

Preferably, the flow rate is a predetermined fixed flow rate. Preferably, the first predefined time period of aerosol particle free air is up to about 10 seconds, the second predefined time period of aerosol particle free air is up to about 10 seconds and the predefined volume of aerosolized particles is up to about 3000 ml. Preferably, the first predefined time period enables a predefined volume of aerosol particle free air, the predefined volume being up to about 6 liters. Preferably, the second predefined time period enables a predefined volume of aerosol particle free air, the predefined volume is up to about 3 liters.

Preferably, the predefined volume of aerosolized particles is introduced into the flow path for a preset time period.

Preferably, the method further comprises steps of measuring and adapting the first predefined time period, the second predefined time period and/or the predefined volume of aerosolized particles based on measurements of at least one health parameter.

The term "pharmaceutical formulation" as used herein, includes active ingredients, drugs, medicaments, compounds, compositions, or mixtures of substances bringing about a pharmacological, often advantageous, effect. It includes food, food supplements, nutrients, medicaments, vaccines, vitamins, and other useful active ingredients. Moreover, the terms, as used herein, include any physiologically or pharmacologically active substances, bringing about a topical or systemic effect in a patient. The active ingredient lending itself to administration in the form of an aerosol can be an antibody, antiviral active ingredient, anti-epileptic, analgesic, anti-inflammatory active ingredient, and bronchodilator or can be an organic or inorganic compound, which without any restrictions can also be a medicament having an effect on the peripheral nervous system, adrenergic receptors, cholinergic receptors, skeletal muscles, cardiovascular system, unstriated muscles, circulatory system, neuronal connections, pulmonary system, respiratory system, endocrine and hormonic system, immune system, reproductive system, skeletal system, food supply system and excretory system, histamine cascade or central nervous system. Suitable active ingredients are for instance polysaccharides, steroids, hypnotics and sedatives, activators, tranquilizers, anticonvulsives (antispasmodics) and muscle35 relaxants, anti-Parkinson-substances, analgesics, anti-inflammatory agents, antimicrobial active ingredients, antimalarial agents, hormones, including contraceptives, symphatocomimetics, polypeptides and proteins producing physiological effects, diuretics, substances regulating the lipometabolism, anti-androgenic active ingredients, antiparasitics, neoplastic and antineoplastic agents, antidiabetics, food and food supplements, growth-promoters, fats, stool-regulators, electrolytes, vaccines and diagnostics.

The invention is particularly suited for inhalation application of different active ingredients, such as the following ones (without being restricted thereto): Insulin, calcitonin, erythropoietin (EPO), factor VII, factor IX, cylcosporin, granulozyte colony stimulating factor (GCSF), alpha-1-proteinase inhibitor, elcatonin, granulocyte macrophage colony stimulating factor (GMCSF), growth hormones, human growth hormone (HGH), growth hormone releasing hormone (GHRH), heparin, low molecular weight heparin (LMWH), interferon alpha, interferon beta, interferon gamma, interleukin-2, luteinizing hormone releasing hormone (LHRH), somatostatin, somatostatin-analogs, including octreotides, vasopressin analogs, follicle stimulating hormone (FSH), insulin-like growth factor, insulintropin, interleukin-I receptor antagonist, interleukin-3, interleukin-4, interleukin-6, macrophage colony stimulating factor (M-CSF), nerve growth factor, parathryoid hormone (PTH), thymosin alpha 1, IIb/IIIa inhibitor, alpha-1 antitrypsin, antibodies against respiratorily syncytic virus, cystic fibrosis transmembrane regulator gene (CFTR), desoxyribonuclease (Dnase), bactericides, permeability increasing protein (BPI), anti-CMV antibodies, interleukin-1-receptor, retinol, retinyl-ester, tocopherols and their esters, tocotrienols and their esters, carotinoids, in particular beta carotin and other natural and synthetic antioxidants, retinol acids, pentamides, albuterolsulfate, metaproterenolsulfate, beclomethasonedipropionate, triamcinolonacetamide, budesonidacetonides, ipratropium bromide, salbutamols, formanilides, flunisolides, fluticasones, cromolyn potassium, ergotamine tartrate and the analogs, agonists and antagonists of the above-mentioned substances.

Moreover, active ingredients can be nucleic acids in the form of pure nucleic acid molecules, viral vectors, associated viral particles, nucleic acids associated with or contained in lipids or a lipid containing material, plasmid DNA or plasmid RNA or other constructs from nucleic acids, which are suitable for cell transfection or cell transformation, in particular in the case of cells of the alveolar region of the lung.

The active ingredient can be present in different forms, such as soluble or insoluble, charged or uncharged molecules, components of molecular complexes or pharmacologically acceptable inactive ingredients. The active ingredient can consist of naturally occurring molecules or their recombinant products, or the molecules can be analogs of the naturally occurring or recombinantly produced active ingredients to which or from which one or more amino acids have been added or deleted. Moreover, the active ingredient can contain attenuated live vaccines or killed viruses for vaccination purposes. If the active ingredient is insulin, it includes naturally extracted human insulin, recombinant human insulin, insulin extracted from cattle and/or swine, recombinant porcine or bovine insulin and mixtures of the above-mentioned insulins. The insulin can be present in a substantially purified form, but can also contain usual commercial extracts. The term "insulin" also includes analogs, to which or from which one or more amino acids of the naturally occurring or recombinant insulin have been added or deleted.

BRIEF DESCRIPTION OF THE DRAWINGS

Some embodiments of the invention will be described with reference to the figures:

FIG. 1 is a perspective view of an embodiment of a system according to the present invention.

FIG. 2 is a front view of the system shown in FIG. 1.

FIG. 3 is an exploded view of components of the system shown in FIG. 1.

FIG. 4 is a top view of the system shown in FIG. 1.

FIG. 5 is a perspective view of another embodiment of a system according to the present invention.

FIG. 6 is a front view of the system shown in FIG. 5.

FIG. 7 is an exploded view of components of the system shown in FIG. 5.

FIG. 8 is a top view of the system shown in FIG. 5.

FIG. 9 is a graph of measurements of forced expiratory volume versus time from experimental data comparing the present invention with prior art device and method.

FIG. 10 is a graph of measurements of heart rate versus time form experimental data comparing the present invention and a prior art device and methods.

FIG. 11 is a cross sectional view of the device illustrated in FIGS. 1-4.

FIG. 12 is a graphical illustration of the functional features of the device illustrated in FIGS. 1-4.

DESCRIPTION OF THE PREFERRED EMBODIMENT

In FIGS. 1 to 4, one embodiment of a system according to the present invention is illustrated. In this embodiment, system A comprises a device 10 according to the invention, a monitor 20 for measuring a health parameter and a base station 30 for receiving the device 10 and/or monitor 20.

As depicted, the device 10 can be hand-held, portable device. The device 10 has a housing with a mouthpiece 11. The mouthpiece 11 may be removed or replaced by a compatible mouthpiece. To this end, a connection is provided in the housing of device 10 for enabling a detachable connection with the mouthpiece 11. Alternatively, mouthpiece 11 may be an integral part of the housing of the device 10. Device 10 is also adapted to receive a cartridge or receptacle 40 holding the pharmaceutical formulation or drug. For example, the housing of device 10 can be manufactured such that cartridge 40 can simply be inserted into the top of the device as shown in FIG. 3.

The monitor 20 can also be a hand-held, portable device as shown. Monitor 20 may also have control buttons for controlling the operations of the monitor and/or a display for showing measured results and/or settings. Monitor 20 can be a spirometer for measuring a lung function parameter, for example the inhalation or the exhalation capacity of the subject.

The base station 30 includes cradles 32, or the like, for holding the device 10 and monitor 20. The base station 30 may also serve as a charger for recharging any batteries provided in device 10 and/or monitor 20. To this end, cradles 32 may include an interface enabling an electronic connection with device 10 or monitor 20. The interface could also enable the transfer of data between the base station 30 and the device 10 or monitor 20. As depicted, base station 30 may also have a display 31 for displaying any desired information or data, for example the status of the base station 30, device 10 and/or monitor 20. Base station 30 may optionally include a slot 34 for receiving a memory card, e.g. a smart card, having data with the subject's aerosol parameters. In this respect, multiple users could use the base station 30 for adapting their inhalation devices 10. Base station 30 may also include an additional reader for reading a storage medium like a memory stick. Although not shown, base station 30 may include communication means for enabling wired or wireless telecommunication and/or data transfer to and from a remote location. The display 31 can optionally include a timer 35 to indicate when to inhale and exhale and a communication means 36.

Figure 1:
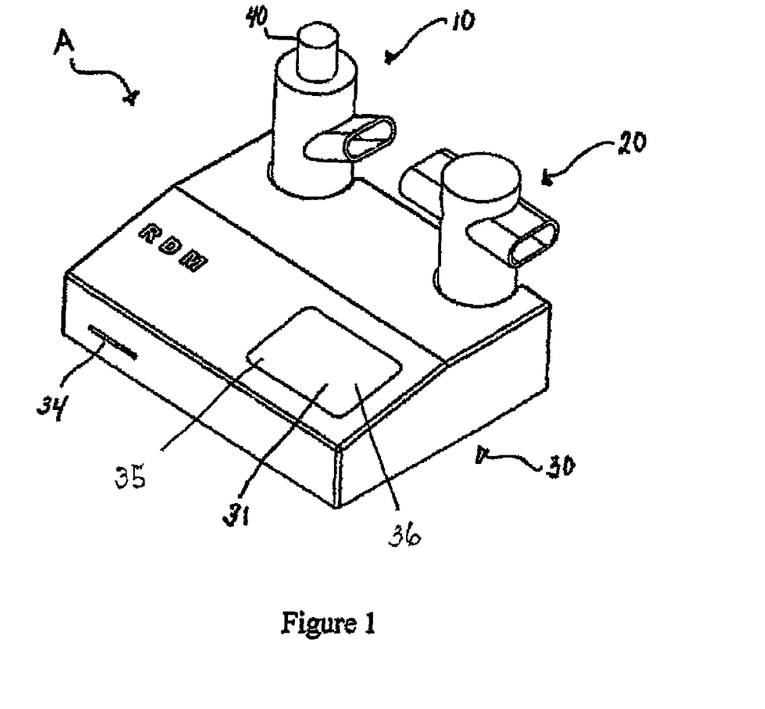
Figure 2:
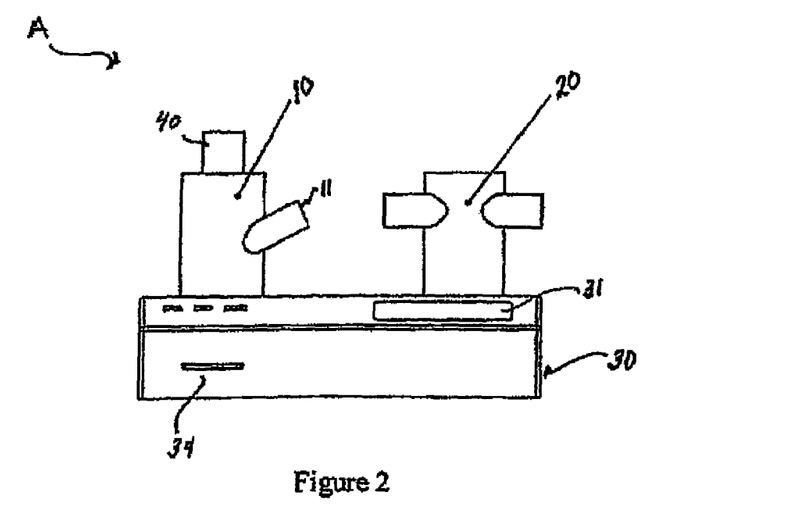
Figure 3:
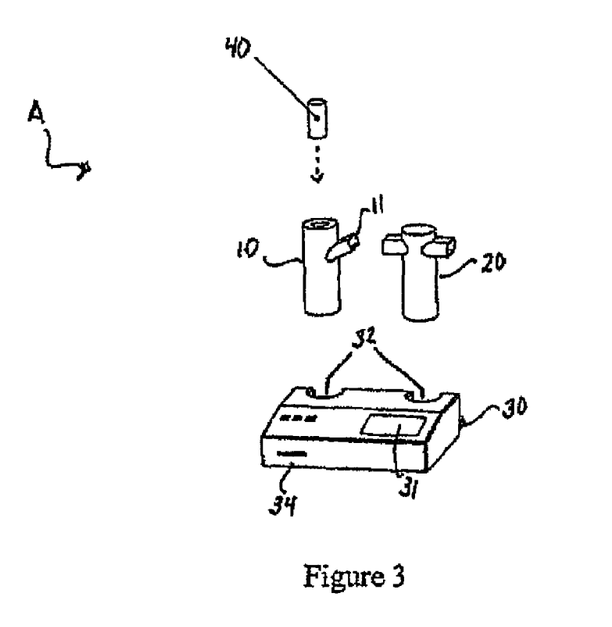
Figure 4:
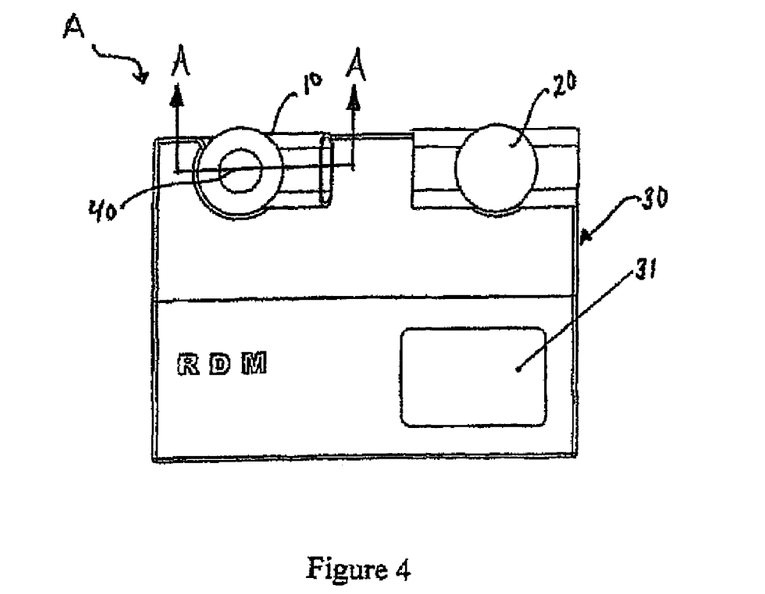
Figure 5:
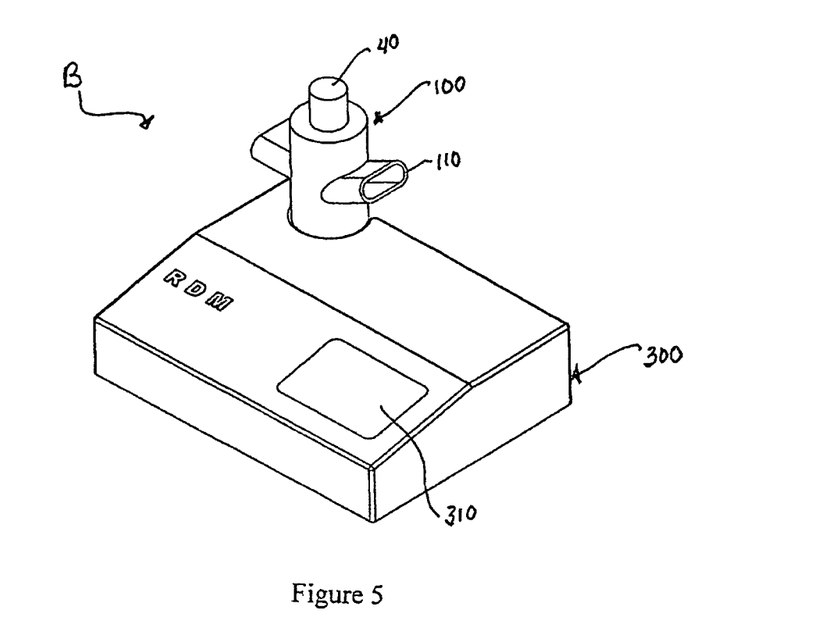
Figure 6:
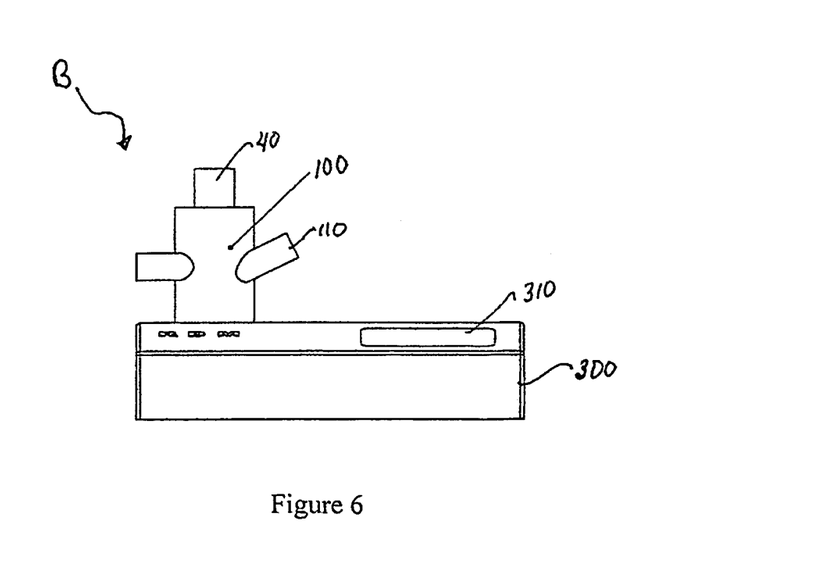
Figure 7:
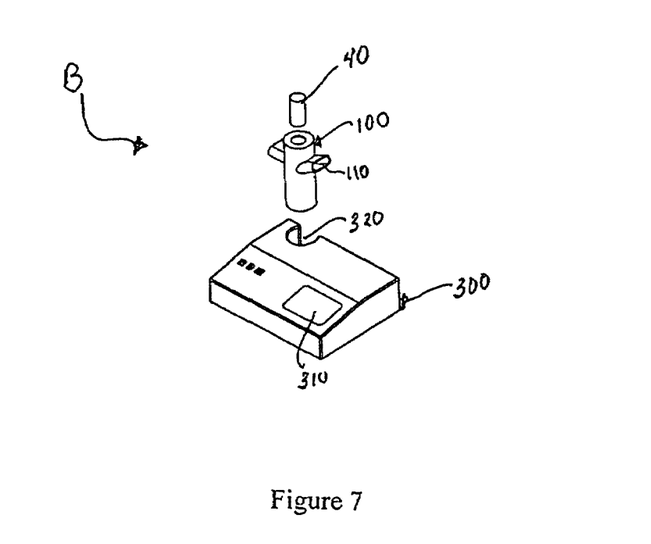
Figure 8:
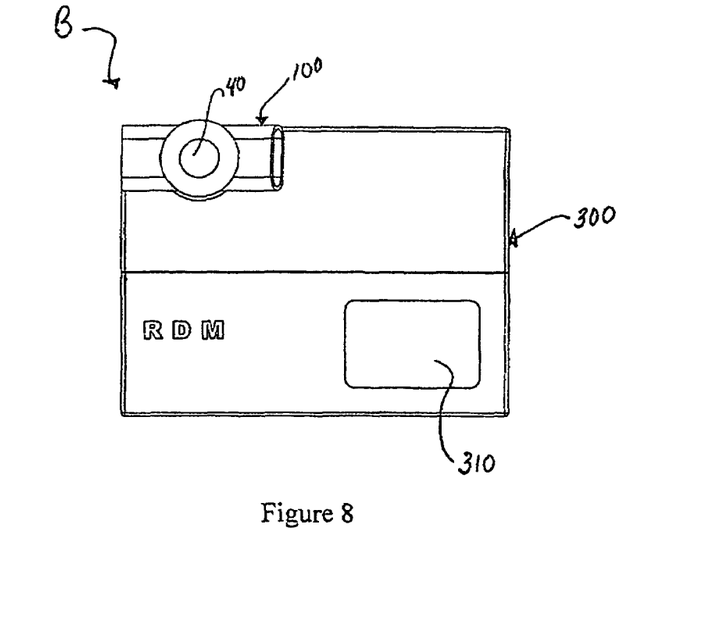

FIGS. 5 to 8 show an alternative embodiment of the system of the present invention. In this embodiment, system B comprises a device 100 according to the invention and a base station 300 for receiving device 100. The device 100 and base station 300 can have the same features as device 10 and base station 30 respectively. Different from device 10, device 100 also comprises a monitor or monitoring means and can function as both inhalation device and health parameter monitor. For example, device 100 can be an integrated inhalation device and spirometer as shown in FIGS. 5 to 8. As shown in FIG. 7, device 100 can also be configured to receive at least one drug cartridge 40.

In FIGS. 1 to 8, exemplary systems are shown for respiratory disease management (RDM). However, modifications of the present system are possible for other types of disease management. Also, variations of illustrated systems A and B are possible. For example, the base station 30 of system A may be used for receiving device 100 having an integrated spirometer and an additional monitor for measuring a health parameter such as a cardio-monitor measuring heart beat rate for example.

An experiment was performed to test the effectiveness of targeting aerosolized particles to specific areas of the lungs using the methods and devices of the present invention. The experiment was made using albuterol, a drug commonly used to treat asthma as an aerosol. Although commonly used in the field of asthma treatment, many patients have reported several undesirable side effects including palpitations, tremors and nervousness. It has been found in the field that the side effects of albuterol are directly related to the dose delivered and absorbed in the blood stream.

Figure 11:
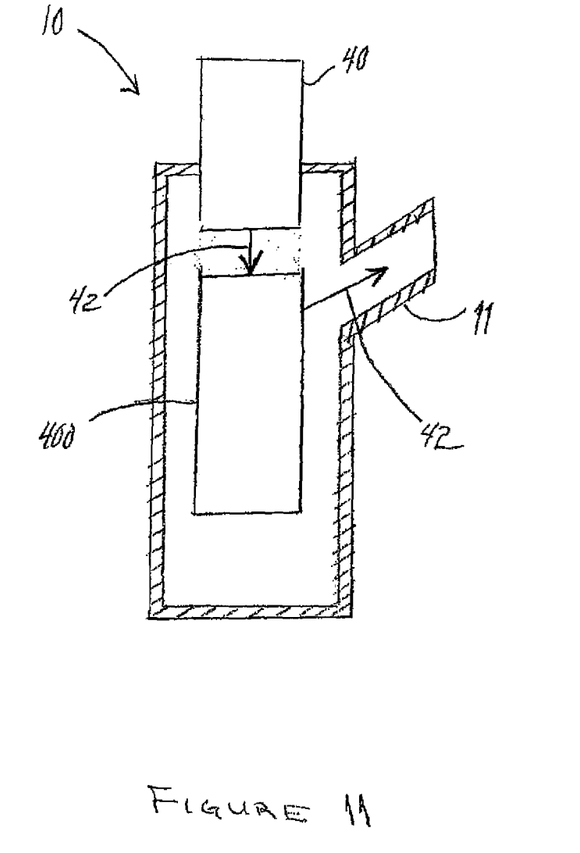
Figure 12:
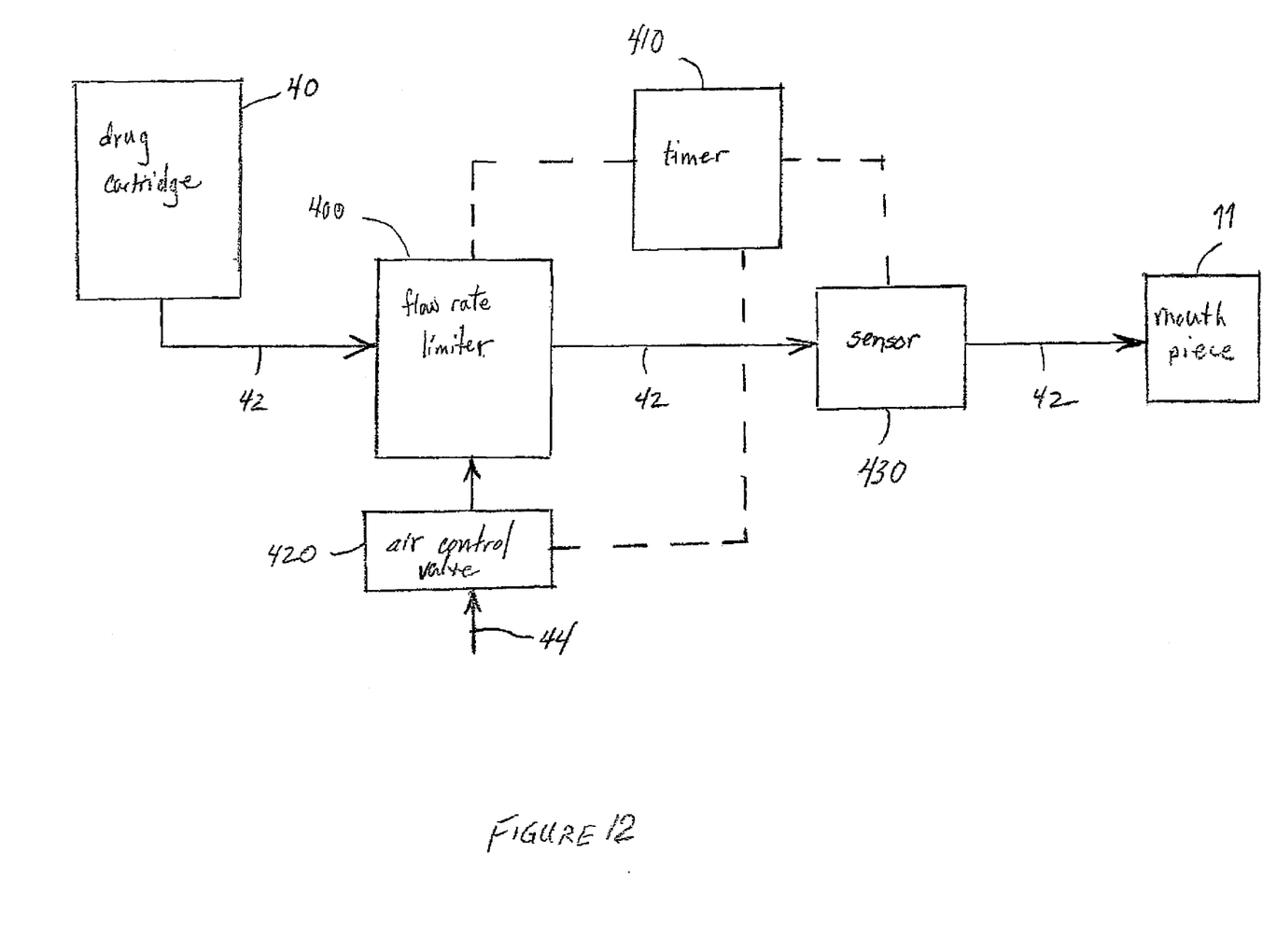

FIG. 11 illustrates a cross sectional view of a device 10 and mouthpiece 11 taken along cross section line A-A and illustrates the flow pathway 42 from the pharmaceutical formulation or drug cartridge 40 to the flow rate limiter 400 and then to the mouth piece 11. FIG. 12 illustrates the functional features that are included in the device 10 and which may or may not include alternative specific structural embodiments as set below. Device 10 includes a flow rate limiter 400. Flow rate limiter 400 is connected to the pharmaceutical formulation or drug cartridge 40 and to the mouth piece 11 via flow pathway 42. Timer 410 controls the flow rate limiter to initiate, once a subject begins inhalation and has inhaled a first predefined time period of aerosol particle free air, a predefined volume of aerosolized particles to be introduced into the flow path, and to initiate after said predefined volume of aerosolized particles a second predefined time period of aerosol particle free air, such that the aerosolized particles are directed to bronchial and/or peripheral airways of the lungs. Device 10 may also include an air control valve 420 is connected to the source of particle free air via particle free air pathway 44. Air control value 420 is typically controlled by the timer may include a piezo-controlled valve, diaphragm-activated motor, solenoid, air piston or a mechanical valve a mechanical switch. Device 10 may also include a sensor 430 for detecting when a subject is inhaling through the flow path. Sensor 430 is also typically, connected to the timer and may include a pressure gauge responsive to suction pressure due to the subject's inhalation, a diaphragm responsive to audible intensity of the inhalation flow rate, said diaphragm preferably being a microphone, mechanical switch or a piezo membrane.

As indication of the degree of bronchodilation, a spirometer was used to measure the forced expiratory volume per sec (FEV1) at several points in time. As an indication of the side effects of the drug, the heart rate of the subject was measured. Tremor effects were measured by a finger accelerometer. For the experiment, a nebulizer was used. The nebulizer was built around a small vibrating disk that has 4,000 laser precision drilled holes in it. The disk was vibrated on the surface of the Albuterol at more than 100,000 times per second. This pulled the liquid through the holes to form droplets of precise uniform size.

In the experiment, data was measured for five different cases; A, B, C, D and E, each having different aerosol parameters:

In Case A, a conventional device and method were used, and no targeting of the aerosolized particles was performed. A 2500 µg albuterol formulation was nebulized, which represents approximately the typical adult dose used in conventional nebulizers for achieving maximal bronchodialation.

In Cases B, C, D and E, the device and methods of the present invention were used.

In Case B, the aerosolized particles were targeted to the large airways of the lungs using a 6-micron diameter particle size and 104 µg albuterol loaded into the device with 50 µg deposited.

In Case C, the aerosolized particles were targeted to the large and small airways of the lungs using a 3.5-micron diameter particle size and 188 µg albuterol loaded into the device with 50 µg deposited.

In Case D, the aerosolized particles were targeted to the alveolar airways of the lungs using a 3.5-micron diameter particle size and 98 µg albuterol loaded into the device with 50 µg deposited.

In Case E, the aerosolized particles were targeted to the large and small airways of the lungs using a 3.5-micron diameter particle size and 282 µg albuterol loaded into the device with 75 µg deposited.

Figure 9:
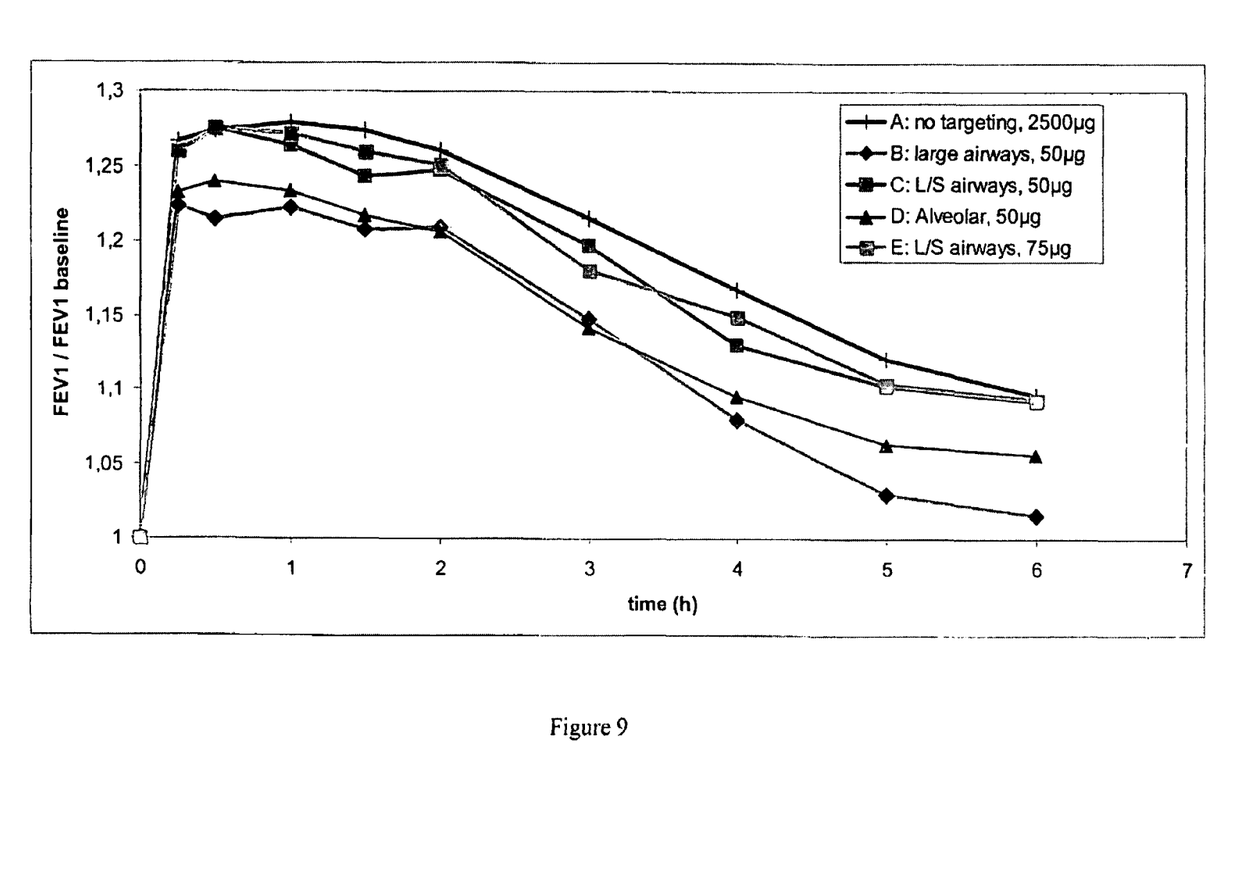
Figure 10:
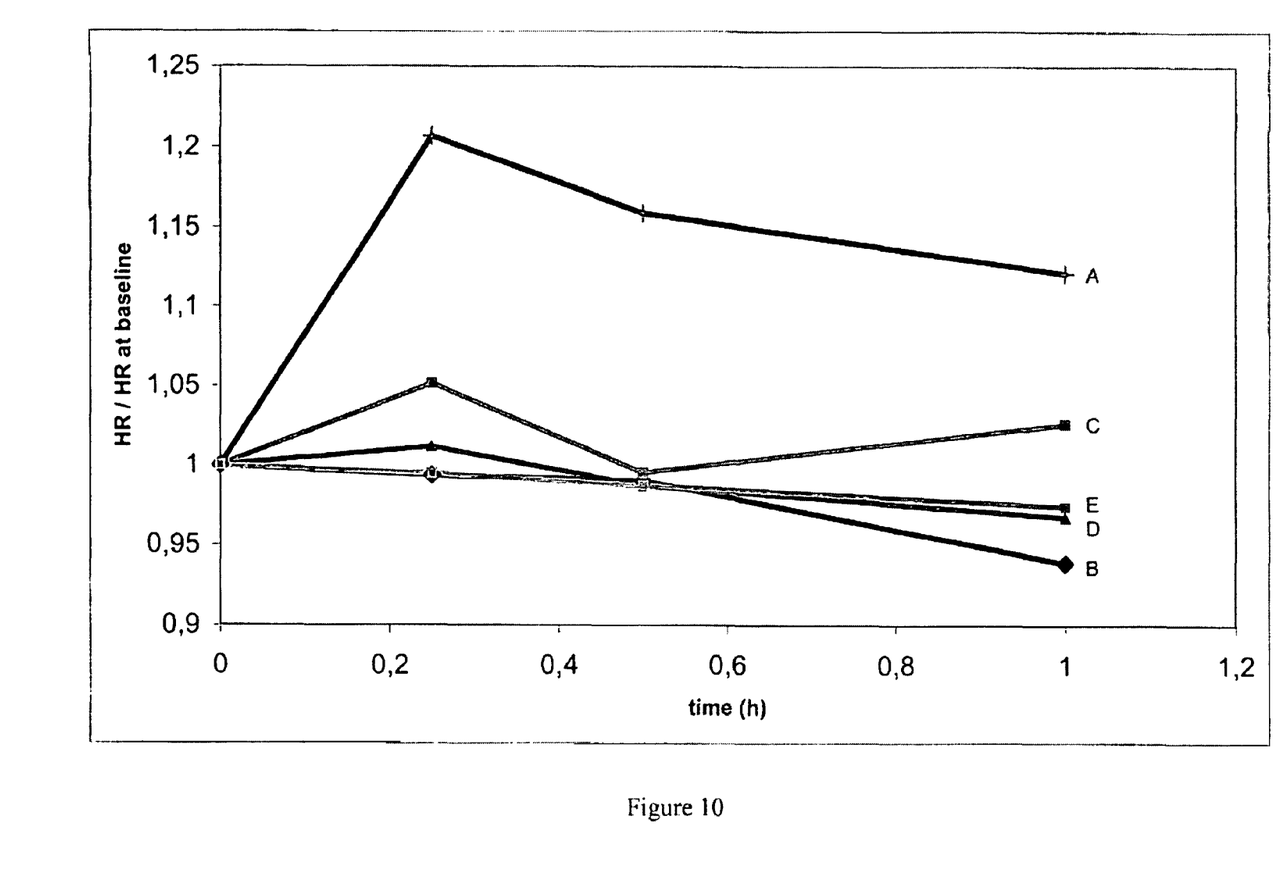

Referring to FIGS. 9 and 10, the experimental results of the measured FEV1 and heart rate over a period of time are depicted for Cases A, B, C, D and E. Although Case A exhibited a maximal bronchodilation, the heart rate significantly increased thereby representing a heart attack risk for the subject.

Case B resulted in a notable bronchodilation, yet significantly less than the degree of bronchodilation achieved with Case A. However, in contrast to Case A, the heart rate remained stabile.

With Case C, a very good bronchodilation was achieved, which was approximately equivalent to that of Case A. In contrast to Case A, the heart rate remained stabile. Also, a significantly lower amount of albuterol was sufficient for achieving similar degree of bronchodilation as that of Case A.

In Case D, the same amount of albuterol was used as Case C. However, the lower region (alveolar) of the lungs was targeted. The degree of bronchodilation was significantly lesser than that of Case A. However, in contrast to Case A, the heart rate remained stabile.

For Case E, the large and small airways were targeted as in Case C. However, the deposited dose of albuterol was increased by 50 percent to 75 µg. Case E resulted in very good bronchodilation with FEV1 measurements being almost equivalent to those of Case A. However, in contrast to Case A, the heart rate remained stabile.

Also, as can be seen in FIGS. 9 and 10, Cases C and E had the same duration of effect as Case A. Cases B, C, D and E lead to less tremor effects as Case A. Hence, the experimental data suggest that, using significantly less than the normal dose, the present invention provides equivalent bronchodilation, equivalent duration of effect and induces less cardiac stimulation and tremor effects In particular, the experimental results show that the efficacy of a pharmaceutical formulation can be notably increased, without involving a significantly increase in dose amounts and side effects, by targeting the aerosolized formulation to certain areas of the lungs using the device of the present invention. This provides valuable advantages for the subject, especially in terms of reducing possible health risks associated with various pharmaceutical formulations. Subjects would benefit by needing only a small percentage of the typical drug dose to attain the same therapeutic effects.

The various embodiments and experimental results presented in the specification are used for the sake of description and clarification of the invention, and thus should not be interpreted as limiting the scope of the invention as such. Moreover, the present invention is realized by the features of the claims and any obvious modifications thereof.

LIST OF REFERENCE NUMERALS

A System
10 device
1 mouthpiece of device
20 spirometer
30 base station
31 display
32 cradle
34 slot for reader
35 timer
36 communication means
40 drug cartridge
42 flow pathway
44 particle free air pathway
B System
100 device
110 mouthpiece of device
300 base station
310 display
320 cradle
Device Features
400 flow rate limiter
410 timer
420 air control valve
430 sensor

The invention claimed is:

1. A device for depositing aerosol particles to specific area of the lungs, the device comprising: a) a flow rate limiter for limiting inhalation flow rate in a flow path to a preset flow rate range; and b) a timer to initiate, once a subject begins inhalation and has inhaled a first predefined time period of aerosol particle free air, a predefined volume of aerosolized particles to be introduced into the flow path, and to initiate after said predefined volume of aerosolized particles a second predefined time period of aerosol particle free air, such that the aerosolized particles are directed to bronchial and/or peripheral airways of the lungs.

2. The device of claim 1, wherein said first predefined time period of aerosol particle free air is up to about 10 seconds, said second predefined time period of aerosol particle free air is up to about 10 seconds and said predefined volume of aerosolized particles is up to about 3000 ml.

3. The device of claim 1, wherein said first predefined time period enables a predefined volume of aerosol particle free air, the predefined volume being about up to about 6 liters.

4. The device of claim 1, wherein said predefined volume of aerosolized particles is introduced into the flow path for a preset time period.

5. The device of claim 1, wherein said second predefined time period enables a predefined volume of aerosol particle free air, the predefined volume being up to about 3 liters.

6. The device of claim 1, wherein the flow rate limiter is responsive to the timer and adapted to seal the flow path after the subject has inhaled the second predefined time period of aerosol particle free air.

7. The device of claim 1, wherein the timer is adapted to indicate to the subject to stop inhaling after the subject has inhaled for the second predefined time period of aerosol particle free air or the device further comprises an indicator to alert the subject to stop inhaling after the subject has inhaled for the second predefined time period of aerosol particle free air.

8. The device of claim 1, further comprising an air control valve for enabling a pre-settable volumetric flow of compressed air.

9. The device of claim 8, wherein said air control valve comprises a piezo-controlled valve, diaphragm-activated motor, solenoid, air piston or a mechanical valve operable with a timer.

10. The device of claim 1, further comprising a sensor for detecting when a subject is inhaling through the flow path.

11. The device of claim 10, wherein said sensor comprises a pressure gauge responsive to suction pressure due to the subject's inhalation.

12. The device of claim 10, wherein said sensor comprises a diaphragm responsive to audible intensity of the inhalation flow rate, said diaphragm being a microphone.

13. The device of claim 10, wherein said sensor comprises a mechanical switch or a piezo membrane.

14. The device of claim 1, wherein the flow rate limiter enables flow rate limitation at low differential pressures, of less than 30 mbar.

15. The device of claim 1, wherein the flow rate limiter is a discretely or continuously variable flow limiter or a controllable valve.

16. The device of claim 1, wherein the flow limiter comprises a housing having at least one aspiration orifice, at least one inhalation orifice, and a flow region with at least one flexible wall disposed therebetween, which region has a cross-section which is adapted to be reduced, as a function of the differential pressure prevailing between said inhalation orifice and said aspiration orifice and of the flexibility of the material of each wall, down to a predefined size for predetermined volumetric maximum inhalation flow.

17. The device of claim 16, wherein said flow region is formed between a central aspiration orifice and inhalation orifices radially surrounding the central aspiration orifice as well as star-shaped webs extending from a common bottom surface to said at least one flexible wall and forming flow passages.

18. The device of claim 1, wherein the flow rate is a predetermined fixed flow rate.

19. The device of claim 1, further comprising a mouthpiece connected in fluid communication with said inhalation flow path.

20. The device of claim 1, further comprising at least one orifice releaseably connected to a source of aerosolized particles.

21. The device of claim 1, further comprising means for aerosolizing solid or liquid particles.

22. The device of claim 21, wherein the means for aerosolizing solid or liquid particles is a nebulizer.

23. The device of claim 1, being adapted to receive at least one receptacle containing an active agent.

24. The device of claim 1, wherein the device is a hand-held, portable device.

25. The device of claim 1, further comprising a controller having a memory for storing a subject's individual parameters and/or aerosol depositing parameters.

26. The device of claim 25, wherein said aerosol depositing parameters comprise the first predefined time period, the second predefined time period and/or the predefined volume of aerosolized particles.

27. The device of claim 1, further comprising a reader for reading a memory means having a subject's individual parameters and/or aerosol depositing parameters stored thereon.

28. The device of claim 1, further comprising a communication means for receiving and/or sending data associated with a subject's individual parameters and/or aerosol depositing parameters.

29. The device of claim 1, further comprising at least one monitor for measuring a health parameter, wherein said device is adaptable in response to measurements from one of said at least one monitor.

30. The device of claim 29, wherein said at least one monitor is a spirometer for measuring a pulmonary function parameter indicative of exhalation and/or inhalation capacity.

31. The device of claim 29, wherein the first predefined time period, the second predefined time period and/or the predefined volume of aerosolized particles are adjusted based on measurements.

32. A system for monitoring aerosol particle deposition, the system comprising: a) the device of claim 1, and b) at least one monitor for measuring a health parameter, wherein said device is adaptable in response to measurements from one of said at least one monitor.

33. The system of claim 32, wherein said at least one monitor is a spirometer for measuring a pulmonary function parameter indicative of exhalation and/or inhalation capacity.

34. The system of claim 32, wherein the first predefined time period, the second predefined time period and/or the predefined volume of aerosolized particles are adjusted based on the measurements.

35. A method for depositing aerosol particles to the central airways of the lungs comprising: a) providing a first predefined time period of aerosol particle free air through a flow path into the lungs at a flow rate within a preset flow rate range; b) delivering a predefined volume of aerosolized particles to be inhaled into the flow path; and c) providing a second predefined time period of aerosol particle free air into the lungs at a flow rate within the preset flow rate range to move the aerosolized particles out of the upper airway region.

36. The method of claim 35, further comprising a step preventing flow through the flow path after providing the second predefined time period of aerosol particle free air.

37. The method of claim 35, further comprising providing indication to the subject to stop inhaling after providing the second predefined time period of aerosol particle free air for the preset time period.

38. The method of claim 35, further comprising detecting when the subject is inhaling through the flow path.

39. The method of claim 35, wherein the flow rate is a predetermined fixed flow rate.

40. The method of claim 35, wherein the first predefined time period enables a predefined volume of aerosol particle free air, the predefined volume being up to about 6 liters.

41. The method of claim 35, wherein the predefined volume of aerosolized particles is introduced into the flow path for a preset time period.

42. The method of claim 35, further comprising the steps of measuring and adapting the first predefined time period, the second predefined time period and/or the predefined volume of aerosolized particles based on measurements of at least one health parameter.

43. The method of claim 35, wherein the first predefined time period of aerosol particle free air is up to about 10 seconds, the second predefined time period of aerosol particle free air is up to about 10 seconds and the predefined volume of aerosolized particles is up to about 3000 ml.

44. The method of claim 35, wherein the second predefined time period enables a predefined volume of aerosol particle free air, the predefined volume being up to about 3 liters.

* * * * *